(12) United States Patent
Grueebler et al.

(10) Patent No.: US 10,675,180 B2
(45) Date of Patent: Jun. 9, 2020

(54) MEMBRANE DELAMINATION DEVICES

(71) Applicant: Novartis AG, Basel (CH)

(72) Inventors: Reto Grueebler, Schaffhausen (CH); Thomas Linsi, Schaffhausen (CH); Rodolfo Wolfer, Schaffhausen (CH); Bogdan Vigaru, Schaffhausen (CH); Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 305 days.

(21) Appl. No.: 15/624,763

(22) Filed: Jun. 16, 2017

(65) Prior Publication Data
US 2017/0360603 A1     Dec. 21, 2017

Related U.S. Application Data

(60) Provisional application No. 62/472,337, filed on Mar. 16, 2017, provisional application No. 62/351,486, filed on Jun. 17, 2016.

(51) Int. Cl.
*A61F 9/007* (2006.01)
*A61F 9/013* (2006.01)

(52) U.S. Cl.
CPC .......... *A61F 9/007* (2013.01); *A61F 9/00709* (2013.01); *A61F 9/00736* (2013.01); *A61F 9/00763* (2013.01); *A61F 9/013* (2013.01)

(58) Field of Classification Search
CPC .............. A61F 9/00709; A61F 9/00763; A61F 9/00736; A61F 9/007; A61F 9/013
See application file for complete search history.

(56) References Cited

U.S. PATENT DOCUMENTS

| | | | |
|---|---|---|---|
| 5,175,528 A | 12/1992 | Choi | |
| 5,350,391 A * | 9/1994 | Iacovelli | A61B 17/320016 606/167 |
| 5,389,104 A * | 2/1995 | Hahnen | A61B 17/1608 606/174 |
| 5,584,845 A * | 12/1996 | Hart | A61B 17/3201 606/174 |
| 5,797,939 A * | 8/1998 | Yoon | A61B 17/122 606/167 |
| 5,911,736 A * | 6/1999 | Dingier | A61B 17/320016 606/208 |
| 5,921,998 A | 7/1999 | Tano et al. | |

(Continued)

FOREIGN PATENT DOCUMENTS

| | | |
|---|---|---|
| CN | 201510417 U | 6/2010 |
| CN | 101637419 B | 11/2011 |

(Continued)

*Primary Examiner* — Phong Son H Dang

(57) ABSTRACT

Various membrane delamination devices for removing proliferative membranes from underling tissues are disclosed herein. In some implementations, the delamination device may include a first shearing part and a second shearing part. One of the first shearing part and the second shearing part may be moveable relative to the other of the first shearing part and the second shearing part. One or more of the shearing parts may include a plurality of teeth formed at a leading edge thereof. A shearing action produced by operation of the shearing parts may be used to sever fibers joining proliferative membranes from an underlying tissue.

6 Claims, 16 Drawing Sheets

(56) References Cited

U.S. PATENT DOCUMENTS

| | | | | |
|---|---|---|---|---|
| 6,086,606 | A * | 7/2000 | Knodel | A61B 17/29 606/174 |
| 6,168,605 | B1 * | 1/2001 | Measamer | A61B 17/320016 606/170 |
| 6,270,508 | B1 * | 8/2001 | Klieman | A61B 17/062 606/147 |
| 6,371,956 | B1 * | 4/2002 | Wilson | A61B 18/1445 606/49 |
| 6,428,539 | B1 | 8/2002 | Baxter et al. | |
| 7,731,728 | B2 | 6/2010 | Glaser | |
| 8,128,649 | B2 * | 3/2012 | Slater | A61B 17/3201 606/205 |
| 8,425,596 | B2 | 4/2013 | Britton et al. | |
| 8,834,501 | B2 * | 9/2014 | Slater | A61B 17/3201 606/174 |
| 9,681,883 | B2 * | 6/2017 | Windgassen | A61B 17/2909 |
| 10,327,799 | B2 * | 6/2019 | Matsuo | A61B 17/3201 |
| 2003/0120305 | A1 * | 6/2003 | Jud | A61B 17/320016 606/205 |
| 2008/0021278 | A1 * | 1/2008 | Leonard | A61B 17/1608 600/129 |
| 2009/0281561 | A1 * | 11/2009 | Kessler | A61B 17/320016 606/174 |
| 2013/0218159 | A1 * | 8/2013 | Kappel | A61B 17/0218 606/45 |
| 2014/0121697 | A1 | 5/2014 | Awh et al. | |
| 2014/0128909 | A1 | 9/2014 | Awh et al. | |
| 2014/0277110 | A1 | 9/2014 | Chow et al. | |
| 2015/0216549 | A1 | 8/2015 | Voic et al. | |

FOREIGN PATENT DOCUMENTS

| | | |
|---|---|---|
| DE | 3921935 A1 | 2/1990 |
| EP | 1216001 B1 | 2/1998 |
| EP | 1278466 A1 | 1/2003 |
| EP | 2825108 A1 | 1/2015 |
| JP | 9313522 A2 | 12/1997 |
| JP | 3101460 B2 | 6/2004 |
| RU | 2122389 C1 | 11/1998 |
| RU | 14509 U1 | 8/2000 |
| RU | 2288682 C1 | 12/2006 |
| RU | 2335269 C1 | 10/2008 |
| RU | 82117 U1 | 4/2009 |
| RU | 106102 U1 | 7/2011 |
| WO | 0182808 A1 | 11/2001 |
| WO | 200644727 A2 | 4/2006 |
| WO | 2013120491 A1 | 8/2013 |
| WO | 2014090244 A1 | 6/2014 |
| WO | 201580677 A1 | 6/2015 |

* cited by examiner

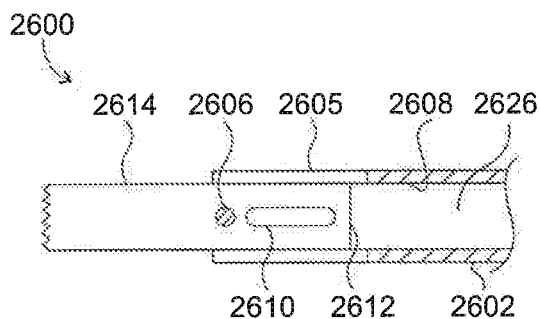
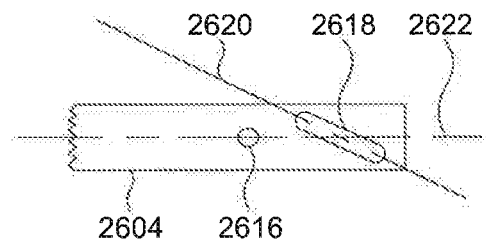
FIG. 26  FIG. 27
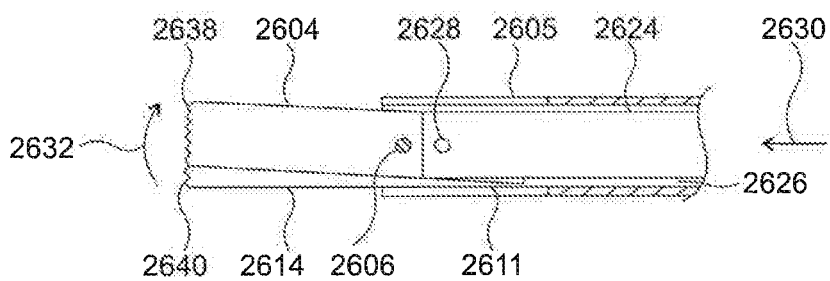
FIG. 28
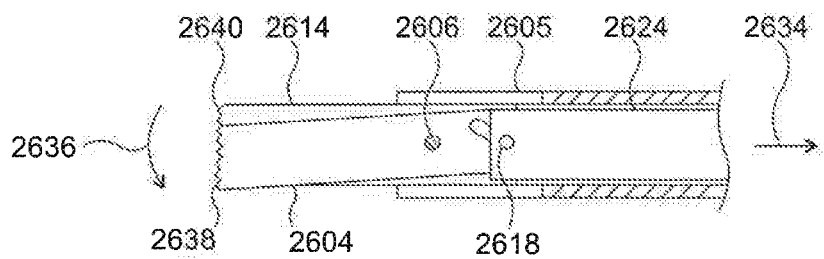
FIG. 29
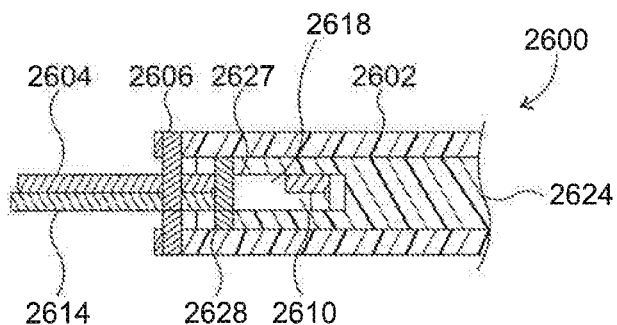
FIG. 30

MEMBRANE DELAMINATION DEVICES

CROSS-REFERENCE TO RELATED APPLICATIONS

This application claims the benefit of U.S. Provisional Application No. 62/352,486, filed Jun. 17, 2016 and U.S. Provisional Application No. 62/472,337, filed Mar. 16, 2017, the entire contents of both being incorporated herein by reference

TECHNICAL FIELD

The present disclosure relates to systems, devices, and methods for removing retinal traction and for delaminating or removing membranes from underlying tissues, such as removal of proliferative membranes or scar tissues that form on the retina as a result of proliferative diabetic retinopathy (PDR) and proliferative vitreoretinopathy (PVR).

SUMMARY

A membrane delamination device may include a first shearing part; a second shearing part pivotably relative to the first shearing part; and a tubular member longitudinally displaceable relative to the first shearing part and the second shearing part. The second shearing part may be laterally moveable in a first lateral direction in response to longitudinal displacement of the tubular member in a first longitudinal direction, and the second shearing part may be laterally moveable in a second lateral direction opposite the first direction in response to longitudinal displacement of the tubular member in a second longitudinal direction opposite the first longitudinal direction.

Movement of the second shearing part in the first lateral direction may generate a biasing force that urges the second shearing part towards the second lateral direction. The second shearing part may be pivotably connected to the first shearing part. The second shearing part may be pivotably connected to the first shearing part via a pinned connection, and the second shearing part may include a biasing member extending proximally from the pinned connection. The biasing member may be elastically deformed in response to movement of the second shearing part in the first lateral direction to generate a biasing force that urges the second shearing part towards the second lateral direction. The second shearing part may include an engagement surface that forms ramp protruding from a lateral side of the second shearing part.

The membrane delamination device may also include a first elongated member and a second elongated member pivotably moveable relative to the first elongated member. The first shearing part may be disposed at a distal end of the first elongated part, and the second shearing part may be disposed at a distal end of the second elongated member. The tubular member may define a lumen through which the first elongated member and the second elongated member extend. Movement of the tubular member in the first longitudinal direction may cause the tubular member to engage the second elongated member to laterally displace the second elongated member in the first lateral direction and elastically deform the second elongated member to generate the biasing force. Movement of the tubular member in a second longitudinal direction may cause the second elongated member to move in the second lateral direction in response to the biasing force. The first elongated member and the second elongated member may form opposing sides of a divided wire. The first shearing part may form a curved shape having a curvature about an axis having a component that is perpendicular to a longitudinal axis of the tubular member. The second shearing part may include a curvature that is complimentary to the curvature of the first shearing part such that the first shearing part and the second shearing part nest together. At least one of the first shearing part or the second shearing part may include a plurality of teeth formed a long a leading edge thereof. At least one of the first shearing part or the second shearing part may include a sharpened leading edge.

A membrane delamination device may include a tubular member defining a lumen extending therethrough and defining a longitudinal axis; a first shearing part extending from a distal end of the tubular member and fixed relative to the tubular member; a second shearing part extending from the distal end of the tubular member and pivotable relative to the first shearing part at a pinned connection; an elongated member disposed in and longitudinally displaceable within the lumen, the elongated member comprising a third slot formed in a distal end thereof; and a pin. The first shearing part may include a first slot extending parallel to the longitudinal axis, and the second shearing part may include a second slot formed at an angle that is oblique to the longitudinal axis. The third slot may receive proximal ends of the first shearing part and the second searing part. The pin may be coupled to the elongated member and extend across the third slot and through the first slot of the first shearing part and through the second slot of the second shearing part. The second shearing part may be pivotable about the pinned connection in a first angular direction in response to a longitudinal movement of the elongated member in a first longitudinal direction, and the second shearing part may be pivotable about the pinned connection in a second angular direction opposite the first angular direction in response to longitudinal movement of the elongated member in a second longitudinal direction opposite the first longitudinal direction.

The first shearing part may have a curved shape that is concave. The second shearing part may have a curved shape that is convex, and the curved shapes of the first shearing part and the second shearing part may produce a biasing force that urges each of the distal ends of the first shearing part and the second shearing part towards each other. The pinned connection may include a second pin that extends through the tubular member, the first shearing part, and the second shearing part. The first shearing part may form a curved shape having a curvature about an axis having a component that is perpendicular to a longitudinal axis of the tubular member. The second shearing part may include a curvature that is complimentary to the curvature of the first shearing part such that the first shearing part and the second shearing part nest together. At least one of the first shearing part or the second shearing part may include a plurality of teeth formed a long a leading edge thereof. At least one of the first shearing part or the second shearing part may include a sharpened leading edge.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIGS. 26-30 illustrate another example delamination device.

DETAILED DESCRIPTION

Figure 1:
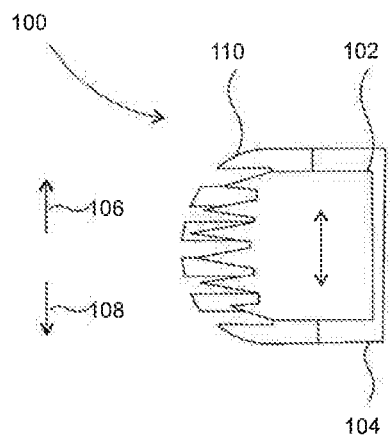
FIG. 1 is a top view of an example delamination device.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present description is made, generally, in the context of ophthalmology, particularly in the context of removing membranes from the retina of an eye and eliminating vitreous traction from the retina by, for example, severing fibers joining the vitreous to the retina. Severing connections between the vitreous and the retina eliminates the traction or pull exerted on the retina by the vitreous, which can result in damage to the retina, such as tears to the retina. However, the scope of the disclosure is not so limited. Rather, the description provided herein may be applied to other areas of the medical arts or elsewhere where removal of a membrane or tissue from an underlying tissue may be desired.

The present disclosure relates to devices and methods for delaminating or removing membranes from underlying tissues, such as removal of proliferative membranes or scar tissues that form on the retina as a result of PDR and PVR as well as removing vitreous traction from the retina. Delamination devices within the scope of the disclosure may be reusable or disposable after a single use.

The delamination devices within the scope of the disclosure include a shearing part that may be made to reside adjacent to delicate tissues, such as the retina. These shearing parts made to reside adjacent to these tissues lack sharp points that may impale the tissues, thereby reducing the risk of injury to these tissues. Further, in many implementations, both shearing parts of the delamination devices within the scope of the disclosure and as described in the context of several of the examples contained herein lack sharp points that could snag or impale the delicate tissues.

Additionally, the delamination devices within the scope of the present disclosure do not apply a vacuum. Thus, the delamination devices eliminate the risk of incarcerating the retina as a result of vacuum pressure.

FIG. 1 shows a top view of an example delamination device 100 that includes a first shearing part 102 adjacent to a second shearing part 104. The first shearing part 102 and second shearing part 104 of the delamination device 100 are generally flat, planar members. However, the scope of the disclosure is not so limited. Rather, in other implementations, the first and second shearing parts may have a curved shape about a longitudinal axis. For example, as explained in more detail below, the first shearing part and second shearing part may be cupped- or U-shaped.

The first shearing part 102 is made to move laterally, as indicated by arrows 106 and 108, relative to the second shearing part 104. This relative movement of the first shearing part 102 relative to the second shearing part 104 generates a shearing action that enables the delamination device 100 to sever fibers that join the undesirous membranes to the retina. In some implementations, the second shearing part 104 may also be made to move relative to the first shearing part 102. However, in use, as the delamination device 100 is made to sever the membrane from the underlying retina, the second shearing part 104 is disposed directly adjacent to the retina. Therefore, movement of the second shearing part 104 relative to the retina is generally undesirable as such movement may result in the second shearing part 104 cutting or otherwise damaging the retina. For example, the relative movement of the second shearing part 104 may generate traction on the retina, which could cause a tear in the retina or cause a portion of the retina to become detached from the eye.

In some implementations, the delamination device 100 may be pneumatically operated. In other implementations, the delamination device 100 may be actuated in other ways, such as electrically, ultrasonic, hydraulically, or manually. Further, any of the example devices described herein may be operated in a similar manner. That is, any of the devices described herein and within the scope of the disclosure may be operated pneumatically, electrically, ultrasonically, hydraulically, or manually. In the context of manual operation of a manually actuated delamination device, a user may actuate a shearing part of the delamination device with a user's hand. Further, any type of actuation power is within the scope of the present disclosure.

Figure 2:
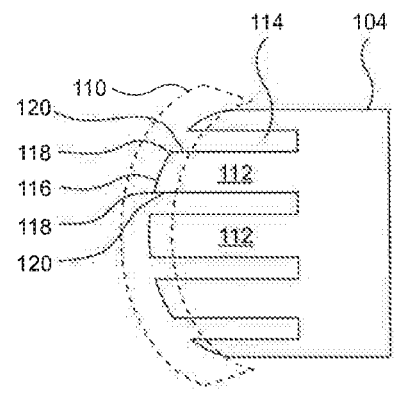
FIG. 2-5 show example teeth designs for use in a shearing part of a delamination device.

FIG. 2 shows the second shearing part 104 of the delamination device 100 shown in FIG. 1. The first shearing part 102 includes a curved leading edge 110, enclosed in area formed by the dotted line, and a plurality of teeth 112 formed along the leading edge 110. The curved leading edge 110 also aids in preventing damage to the retina. Rectangular slots 114 are formed between adjacent teeth 112, and a distal edge 116 of each tooth 112 forms a sharp point 118 with adjacent walls 120 of each tooth 112.

Figure 3:
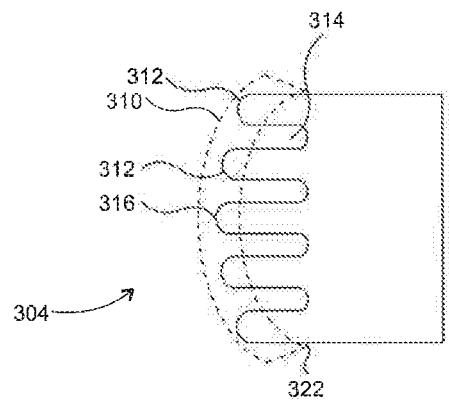
Figure 4:
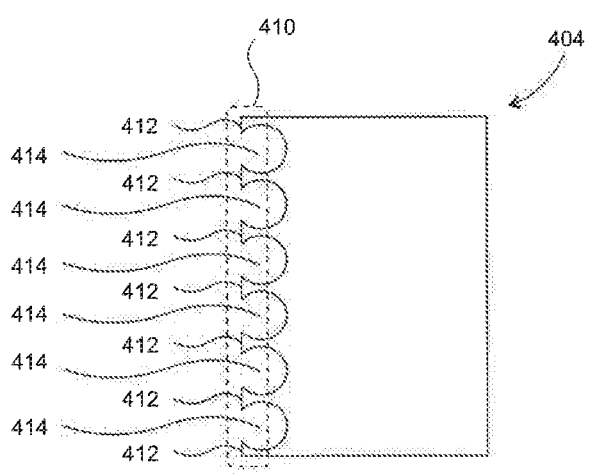

FIGS. 3 and 4 illustrate other designs of the second shearing part 104. Similar to the second shearing part 104 shown in FIGS. 1 and 2, the second shearing part 304 shown in FIG. 3 also includes a curved leading edge 310, and a plurality of teeth 312 formed along the leading edge 310. Here, the teeth 112 have rounded distal edges 316. Additionally, the proximal ends 322 of slots 314 formed between adjacent teeth 312 are also rounded. The rounded distal edges 316 and proximal ends 322 also aid in preventing injury to the retina by reducing push-out forces (e.g., forces generated with the closing of scissors that produce traction on the retina) and by eliminating sharp points that could become ensnared upon the surface of the retina.

The second shearing part 404 shown in FIG. 4 includes a straight leading edge 410 that includes a plurality of teeth 412 formed by circular slots 414 formed into the leading edge 410. The teeth 412 also decrease chances of injury to the retina, as the shape of the teeth 412 as a result of the circular slots 414 produce a pull-in force that counteracts the push-out force associated with shearing.

FIGS. 2-4 show examples of the second shearing parts of a delamination device that have different shapes. Further, FIG. 1 shows the first shearing part 102 and the second shearing part 104 having different shapes. However, the first shearing part and the second shearing part may have the same shape. For example, in some implementations, the first and second shearing parts may have the same shape that corresponds to any one of the shapes illustrated in FIGS. 2-4. Still further, the shapes of the first shearing part and the second shearing part may be different such that either the first shearing part or the second shearing part may have any of the shapes illustrated in FIGS. 2-4.

Figure 5:
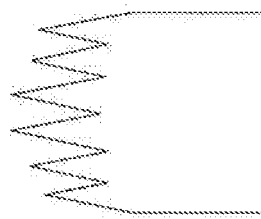
Figure 6:
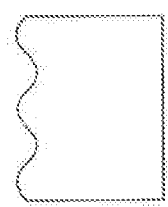
FIGS. 6-10 show example leading edge designs for use in a shearing part of a delamination device.
Figure 7:
Figure 8:
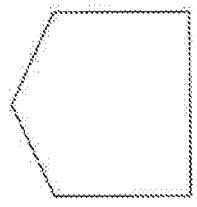
Figure 9:
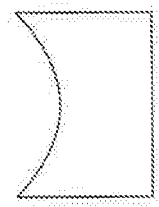
Figure 10:
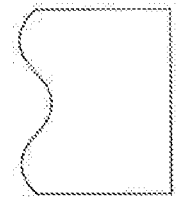

FIG. 5 shows the example first shearing part 102 as illustrated in FIG. 1. In some instances, the curvature or shape of the leading edge of the first shearing part and the second shearing part correspond to each other. That is, if the first shearing part has a curved leading edge, the leading edge of second shearing part is also curved. Similarly, if the leading edge of the first shearing part is straight, the leading edge of the second shearing part is also straight. Further, the shapes of the leading edges of the first and second shearing parts are not limited to curved or straight. Rather, the shape of the leading edges of the first and second shearing parts may have any desired shape. For example, FIGS. 6-10 show example leading edges shapes that may be applied to either or both of the first shearing part or the second shearing part. Particularly, FIG. 6 shows an undulating or sinusoidal leading edge shape. FIG. 7 illustrates a concave V-shaped leading edge, and FIG. 8 shows a convex V-shaped leading edge. FIG. 9 illustrates a concave crescent or arc-shaped leading edge. FIG. 10 shows a leading edge having a series of triangular projections with rounded tips.

Figure 16:
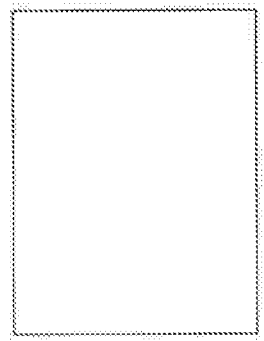
FIGS. 16-18 show additional leading edges designs for use in a shearing part of a delamination device.
Figure 17:
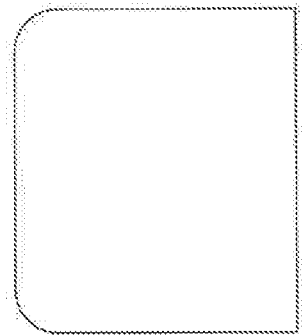
Figure 18:
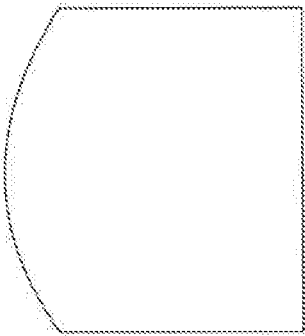

It is noted that FIGS. 6-10 show the general shape of the leading edge and do not show the teeth that may be formed therein. However, it is within the scope of the disclosure that one or both of the first shearing part and the second shearing part may not include teeth formed along the leading edge. FIGS. 16-18 show additional examples of leading edges that may be applied to either or both of the first and second shearing parts. Shearing parts having leading edges according to any shape described in the present disclosure may include or omit teeth therefrom. Moreover, any teeth formed therein may have any desired shape. Further, while the present disclosure provides numerous examples of leading edges of a shearing part, the scope is not so limited. Rather, a leading edge may have any desired shape.

Figure 11:
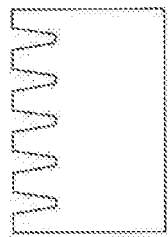
FIG. 11-14 show additional tooth designs for use in a shearing part of a delamination device.
Figure 12:
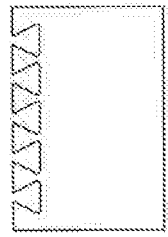
Figure 13:
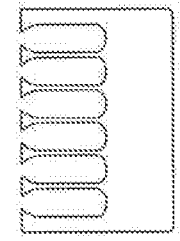

The teeth formed in and along the leading edges may also have a variety of shapes. FIGS. 11-13 show a variety of tooth and slot shapes. For example, FIG. 11 shows teeth having chamfered distal ends and triangular-shaped slots having rounded proximal ends. FIG. 12 also shows triangular slots with the slots inverted compared to those of FIG. 11. The corners of the slots shown in FIG. 12 are rounded. FIG. 13 shows elongated slots with rounded distal and proximal ends.

Figure 41:
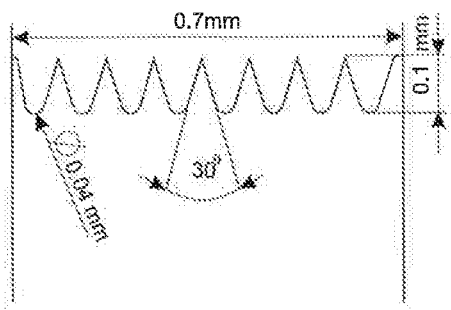
FIGS. 41-43 show additional teeth designs that may be formed along a leading edge of a shearing part.
Figure 42:
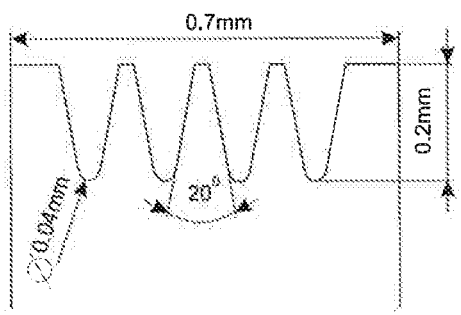
Figure 43:
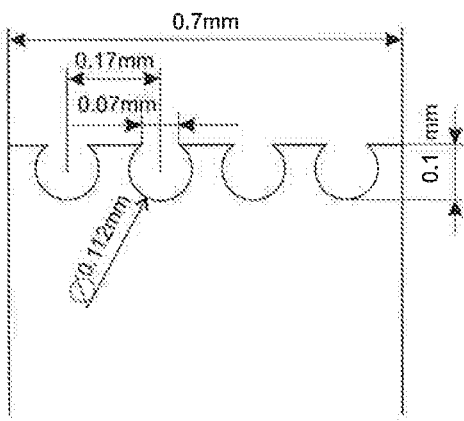

FIGS. 41-43 show additional teeth that may be formed along a leading edge along with example dimensions associated therewith. FIG. 41 shows teeth having pointed ends with triangular-shaped slots having rounded proximal ends. FIG. 42 shows teeth having chamfered distal ends with triangular-shaped slot having rounded proximal ends. FIG. 43 shows teeth having chamfered tips with circular slots formed in-between. It is believed that the shape of the teeth shown in FIG. 43 would provide a pull-in force, as opposed to a push-out force.

While the present disclosure provides numerous examples of both the design of teeth formed in shearing part as well as the number of those teeth formed therein, the number of teeth that may be formed may be a function of both the size of the shearing part as well as the geometry and size of the teeth. In some implementations, the number of teeth formed in a shearing part may be ten teeth. In other implementations, the number of teeth may be two. Again, though, the scope of the disclosure is not so limited, and any number of teeth may be formed in a shearing part.

Figure 14:
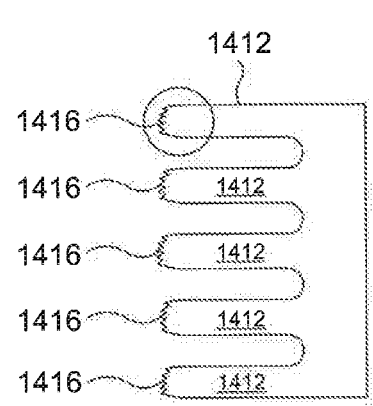
Figure 15:
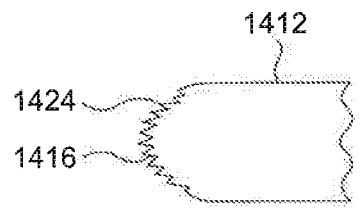
FIG. 15 shows a surface features formed a long a leading edge of a tooth.

The distal end of one or more teeth may also have a texture or contour formed therein. As shown in FIGS. 2-3, the distal end of the teeth form a smooth, continuous edge, whether curved or straight. FIG. 14, though, shows a shearing member 1400 having teeth 1412 with distal edges 1416 thereof with a contour formed therein. While the distal edges 1416 of the teeth 1412 have a generally rounded profile, a zig-zag shaped contour 1424 (shown in detail in FIG. 15) is formed along the distal edge 1416. Although a zig-zag shape is illustrated, the distal edges of the teeth may have any desired shape. Further, the shapes of one of the first shearing part or second shearing part may be different or vary from the corresponding shapes formed in the other of the first shearing part or second shearing part.

Any of the shearing parts described herein may be coated with silicon carbide (SiC) or diamond, such as, for example, using physical vapor deposition. The applied coatings may reduce friction and increase surface hardness. As a result, the delamination devices having such coatings may reduce or eliminate production of metal particles during operation.

Figure 19:
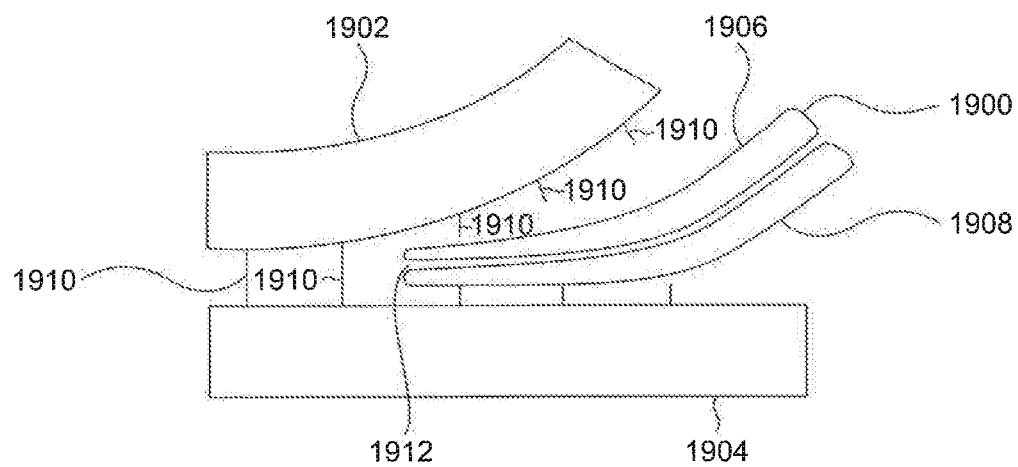
FIG. 19 is a schematic, lateral view showing an example delamination device severing a membrane from an underlying tissue.

FIG. 19 is a schematic side or elevation view of an example delamination device 1900 severing a membrane 1902 from an underlying retina 1904. Lateral shearing movement of the first shearing part 1906 (in a direction into and out of the plane of FIG. 19) relative to the second shearing part 1908 severs fibers 1910 joining the membrane 1902 to the retina 1904 while reducing traction exerted on the retina 1904. In some implementations, lateral movement of the second shearing part 1908 is prevented or substantially reduced. That is, substantially reducing lateral movement of the second shearing part means that lateral movement of the second shearing part for the purpose of severing the fibers is reduced such that lateral movement of the second shearing part is movement unrelated to the shearing action of the delamination device. Thus, movement of second shearing part would be the result of repositioning the delamination device to another area relative to the retina such as to continue removal of the membrane.

In FIG. 19, a gap 1912 is shown between the first and second shearing parts 1906 and 1908. While one or more of the implementations described herein may utilize a gap formed between a first shearing part and a second shearing part, the scope of the disclosure is not so limited. In some instances, all or a portion of adjacent surfaces of the first and second shearing parts may contact each other during all or part of the movement of the first and second shearing parts relative to each other. For example, in some instances, adjacent surfaces of the first and second shearing parts along their respective leading edges may contact each other during articulation of the delamination device.

Figure 20:
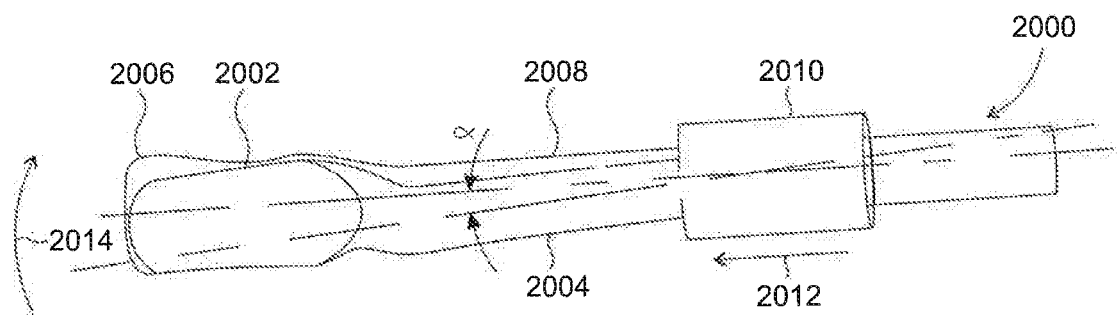
FIGS. 20 and 21 show an example mechanism for moving a first shearing part relative to a second shearing part.
Figure 21:
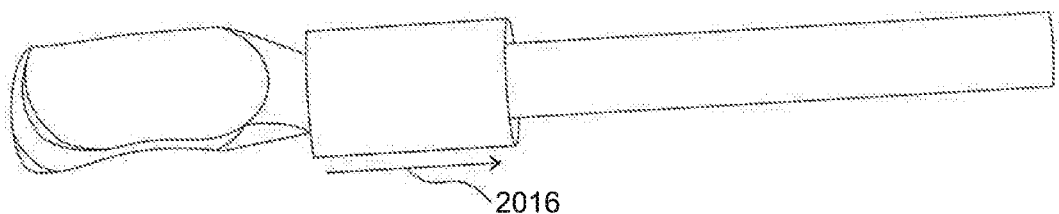

FIGS. 20 and 21 show an example mechanism for moving the first shearing part relative to the second shearing part. FIGS. 20-21 show an example delamination device 2000 that includes a first shearing part 2002 formed at the distal end of a first elongated member 2004 and a second shearing part 2006 formed at the distal end of a second elongated member 2008. The first and second shearing parts 2002 and 2006 may have a cupped shaped such that the first shearing part 2002 nests within the second shearing part 2006. In other implementations, the first and second shearing parts 2002 and 2006 may have shapes other than a cupped shape. For example, in some implementations, the first and second shearing parts 2002 and 2006 may have a flat or planar shape.

Although FIGS. 20 and 21 illustrate the first and second shearing parts 2002 and 2006 do not include teeth formed in their respective leading edges, the scope of the disclosure is not so limited. Rather, either one or both of the leading edges of the first shearing part 2002 or second shearing part 2006 may have teeth formed therein. The shape and size of the teeth and slots formed between adjacent teeth may be any desired size and shape and may include any of the teeth and slot designs described herein.

In some instances, the first elongated member 2004 and the second elongated member 2008 may be separate components that are joined together such as, for example, by a pin joint, a weld joint, or in some other manner. In some instances, the first elongated member 2004 and the second elongated member 2008 may be opposing sides of a wire that has been divided, such as by, for example, electron discharge machining, laser cutting, or in some other manner. In such instances where the first elongated member 2004 and the second elongated member 2008 form opposing sides of a wire, one of the first elongated member 2004 or second elongated member 2008 may be bent relative to the other. Thus, in some implementations, the second elongated member 2008 may remain aligned with the remainder of the wire, which may form part of remainder of the delamination device 2000, while the first elongated member 2004 may be angularly disposed relative to the second elongated member 2008.

The delamination device 2000 also includes a tube 2010 that is moveable relative to the first elongated member 2004 and the second elongated member 2008. As shown in FIG. 20, in a first position, the first elongated member 2004 and the second elongated member 2008 are obliquely arranged. As shown, the first elongated member 2004 and second elongated member 2008 define an angle α. When the tube 2010 is displaced from a first position distally in the direction of arrow 2012, the first elongated member 2004 and the first shearing part 2002 pivot according to arrow 2014 relative to the second elongated member 2008 and second shearing part 2006, repositioning the first shearing part 2002 relative to the second shearing part 2006, as shown in FIG. 21. When the tube 2010 is moved in the direction of arrow 2016, shown in FIG. 21, opposite the direction of arrow 2012, the first elongated member 2004 and first shearing member 2002 returns to its initial position relative to the second elongated member 2008 and second shearing member 2006, as shown in FIG. 20. Further, in some implementations, the first shearing part 2002 may include a bend that biases the first shearing part 2002 towards the second shearing part 2006. This bias provides contact between the first shearing part and second shearing part 2006 during actuation of the delamination device 2000 to ensure cutting of the fibers connecting a membrane to the retina, for example.

Figure 22:
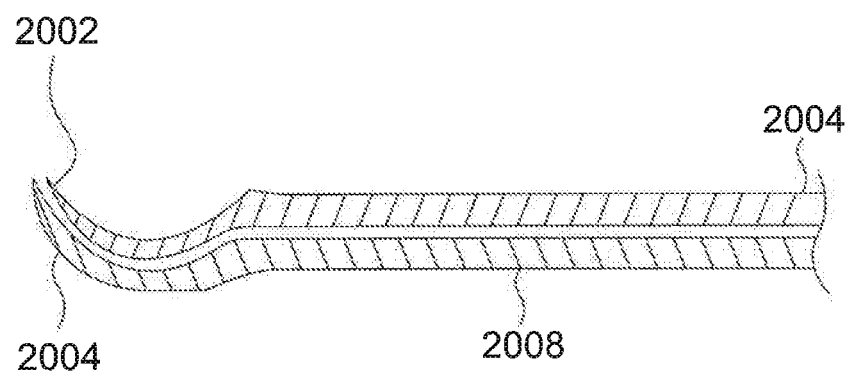
FIG. 22 shows a cross-sectional side view of first and second elongated members and associated first and second shearing parts of the example delamination device shown in FIGS. 20 and 21.

FIG. 22 shows a cross-sectional side view of the first and second elongated members 2004 and 2008 and the associated first and second shearing parts 2002 and 2006. One or more of the first and second elongated members 2004 and 2008 and first and second shearing parts 2002 and 2006 may be formed from a metal, such as stainless steel or titanium, a polymer, such as polypropylene, or any other suitable or desirable material.

In addition to being used to delaminating a membrane or removing vitreous traction by moving the first shearing part 2002 relative to the second shearing part 2006, the delamination device 2000, as well as any of the other delamination devices described herein, may be used as a spatula, such as when the shearing parts are not being moved relative to each other.

Figure 23:
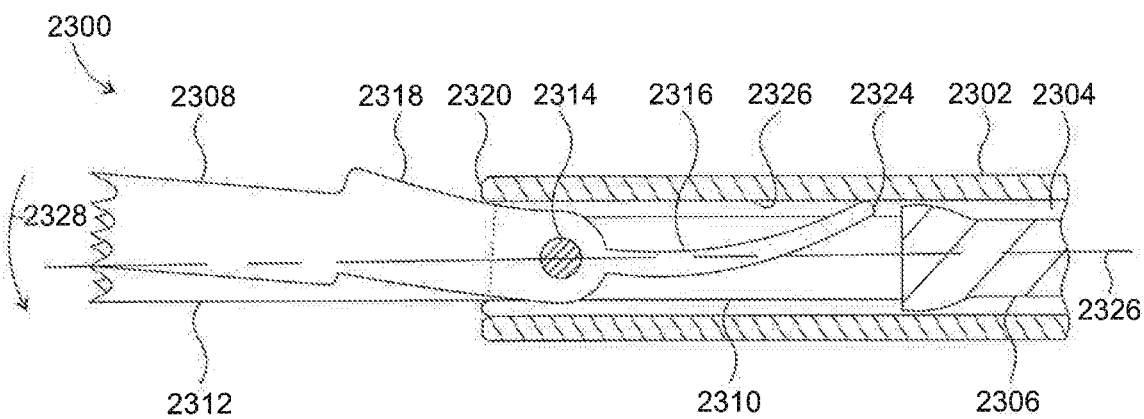
FIGS. 23 and 24 show partial cross-sectional top views of another example delamination device.
Figure 24:
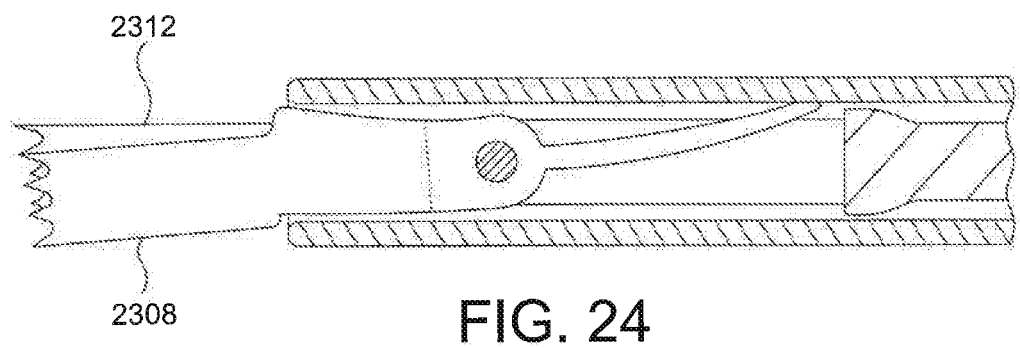

FIGS. 23 and 24 show a partial cross-sectional view of another example delamination device 2300. The delamination device 2300 includes a tubular member 2302 defining a lumen 2304 and an elongated member 2306 extending through the lumen 2304, a first shearing part 2308 and a second shearing part 2312. A second shearing part 2312 is formed on a distal portion 2310 of the elongated member 2306. A first shearing part 2308 is attached to the distal portion 2310 of the elongated member 2306 such that a first shearing part 2308 is pivotable relative to the second shearing part 2321. In some implementations, the second shearing part 2312, distal portion 2310, and the elongated member 2306 may be a single, unitary component. In other implementations, one or more of the second shearing part 2312, the distal portion 2310, and the elongated member 2306 may separate components that are coupled together. In some instances, the first shearing part 2308 may be attached to the distal portion 2310 via a pinned connection 2214. The first shearing part 2308 also includes a biasing member 2316 formed at a proximal end of the first shearing part 2308 and an engagement surface 2318. In some implementations, the engagement surface 2318 may define a ramp that protrudes from a side of the first shearing part 2308, as shown in FIGS. 23 and 24. The biasing member 2316 is operable to bias the first shearing part 2308 in a first lateral position, as shown in FIG. 23. The engagement surface 2318 is operable to contact a distal end 2320 of the tubular member 2302, which causes the first shearing part 2308 to be pivoted about the pinned connection 2314 and displaced from first lateral position into a second lateral position as shown, for example, in FIG. 24.

As indicated above, the second shearing part 2312 is formed at a distal end of the distal portion 2310. As shown in FIGS. 23 and 24, the second shearing part 2312 is fixed relative to the distal portion 2310. Thus, the second shearing part 2312 may have a fixed position on the elongated member 2306. In some implementations, a distal end of the first shearing part 2308 may extend distally beyond a distal end of the second shearing part 2312. In other implementations, the distal ends of the first and second shearing parts 2308 and 2312 may terminate at the same location.

In the example illustrated, the tubular member 2302 may be moveable relative to the elongated member 2306. Particularly, the tubular member 2302 may be reciprocated relative to the elongated member 2306. Thus, in some instances, the tubular member 2302 may be made to reciprocate over and relative to the elongated member 2306. For example, during operation of the delamination device 2300, such as when the delamination device 2300 has a fixed position relative to a surface, e.g., the surface of a retina, the second shearing part 2312 remains stationary relative to the surface as the tubular member 2302 is reciprocated relative to the elongated member 2306. Consequently, the second shearing part 2312 may be kept stationary relative to a retinal surface during actuation of the delamination device 2300.

In operation, the first shearing part 2308 is pivotably oscillated relative to the second shearing part 2312. The oscillating movement of the first shearing part 2308 relative to the second shearing part 2312 functions to sever a membrane from the underlying retina as illustrated, for example, in FIG. 19. FIG. 23 shows the tubular member 2302 in a retracted position. With the tubular member 2302 in the retracted position, a proximal end 2324 of the biasing member 2316 engages an internal surface 2326 of the tubular member 2302 to cause the first shearing part 2308 to be pivotably disposed in the first lateral position, as show in FIG. 23. When the tubular member 2302 is extended distally, the distal end 2320 of the tubular member 2302 engages the engagement surface 2318 to cause the first shearing part 2308 to be pivoted about the pinned connection 2314 in the direction of arrow 2328. As the tubular member 2302 continues to be extended distally, not only is the first shearing part 2308 pivoted about the pinned connection 2314, but also the biasing element 2316 is elastically deformed, which generates a biasing force that urges the first shearing part 2308 back towards the first lateral position.

With the tubular member 2302 in a fully extended position, the first shearing part 2308 is located in the second lateral position shown in FIG. 24. As the tubular member 2302 is retracted back to its fully retracted position shown in FIG. 23, the first shearing part 2308 is urged back into the first lateral position as a result of the bias force generated by the elastically deformed biasing element 2316. In the example shown in FIGS. 23 and 24, the second shearing part 2312 remains stationary with respect to an external reference. For example, when present within an eye adjacent to the retina, the second shearing part 2312 remains stationary relative to the retina even as the first shearing part 2308 is reciprocated as described above.

Figure 25:
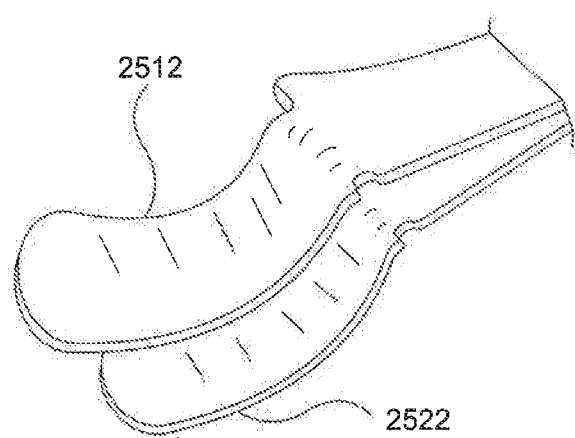
FIG. 25 shows example shearing parts having a curved shape.

FIG. 25 shows first and second shearing parts 2512 and 2522 that may be used in place of the first and second shearing parts 2308 and 2312 included in the delamination device 2300 shown in FIGS. 23 and 24. The example first and second shearing parts 2512 and 2522 include a curvature formed respectively therein. The curvature of the first and second shearing parts 2512 and 2522 may be formed about an axis that is perpendicular or substantially perpendicular to the longitudinal axis of the delamination device, such as the longitudinal axis 2326 shown in FIG. 23. Additionally, although the first and second shearing parts 2512 and 2522 are illustrated as omitting teeth formed in their respective leading edges, one or more teeth may be formed in other implementations of the first and second shearing parts 2512 and 2522. Further, the shape of the shearing parts, the number and shape of the teeth, and the shape of gaps formed between adjacent teeth may be selected to be any desired shape or number, including any of the number, size, or shape of teeth or gaps disclosed herein or size or shape of the shearing members described herein.

FIGS. 26-30 illustrate another example delamination device 2600 having a first shearing part 2604 and a second shearing part 2614. FIG. 26 is a partial cross-sectional view the delamination device 2600. In FIG. 26, a tubular member 2602 and the second shearing part 2614 are illustrated. The second shearing part 2614 may be fixedly attached to the tubular member 2602. A pivot pin 2606 extends through the second shearing part 2614. In some instances, the pivot pin 2606 may extend through the tubular member 2602 and be fixed thereto. In other instances, opposing ends of the pivot pin 2606 may be fixed to an inner surface 2608 of the tubular member 2602. A slot 2610 may be formed in the second shearing part 2614. The slot 2610 may extend from a proximal end 2612 of the second shearing part 2614.

FIG. 27 shows the first shearing part 2604 of the delamination device 2600. The first shearing part 2604 includes an aperture 2616 through which the pivot pin 2606 extends. The first shearing part 2604 also includes a slot 2618 formed therein. The slot 2618 extends along a first axis 2620 that is oblique to a longitudinal axis 2622 of the first shearing part 2604.

FIGS. 28 and 29 show partial cross-sectional top views of the delamination device 2600 with the first and second shearing parts 2604 and 2614 assembled together. As shown, an elongated member 2624 is disposed within a lumen 2626 of the tubular member 2602 and is operable to be reciprocated within the lumen 2626. Proximal ends of the first shearing part and second shearing part 2604 and 2614 are received into a slot 2627 (shown in FIG. 30) formed in a distal end of the elongated member 2624. A pin 2628 extends through the elongated member 2624, across the slot 2627, and is received within the slot 2618 formed in the first shearing part 2604. The pin 2628 may also be received in the slot 2610 formed in the second shearing part 2614. In other implementations, the pin 2628 may be integrally formed with the elongated member 2624.

As the elongated member 2624 is reciprocated, as shown in FIGS. 28 and 29, the pin 2628 rides along the slot 2618. Because of the oblique angle of the slot 2618 relative to the longitudinal axis 2622, movement of the pin 2628 within the slot 2618 causes the first shearing part 2604 to pivot about the pin 2606. For example, in FIG. 28, displacement of the elongated member 2624 in the direction of arrow 2630 into an extended position, such as a fully extended position, causes the first shearing part 2604 to be pivoted about the pin 2606 in the direction of arrow 2632. Similarly, displacement of the elongated member 2624 in the direction of arrow 2634 into a retracted position, such as a fully retracted position, causes the first shearing part 2604 to be pivoted about the pin 2606 in the direction of arrow 2636. Thus, reciprocation of the elongated member 2624 cause a distal end 2638 of the first shearing part 2604 to move relative to a distal end 2640 of the second shearing part 2614, resulting in a shearing action that may be used to separate a membrane from an underlying retina. The tubular member 2602 may include a longitudinally extending slot 2605. The slot 2605 provides a relief to receive a proximal end 2611 of the first shearing part 2604 as the first shearing part 2604 is reciprocated relative to the pin 2606.

Although the first and second shearing parts 2604 and 2614 of the delamination device 2600 are shown as being flat and each having teeth formed at their respective leading edges, the scope of the disclosure is not so limited. Rather, the first and second shearing parts 2604 and 2614 may, in part or in whole, have a curvature, such as a cupped shape. This cupped shape may be similar to that shown in FIG. 20, 21, 22, or 25. Also, one or more of the first or second shearing parts 2604, 2614 may omit teeth. Further, any teeth and gaps formed between adjacent teeth may be any desired shape, including one or more of the types described herein. Also, the shapes of the first and second shearing parts 2604 and 2614 may have any desired shape, including one or more of the shapes described herein.

FIG. 30 is a lateral cross-sectional view of the delamination device 2600 showing the proximal ends of the first and second shearing parts 2604 and 2614 received into the slot 2627 formed in a distal end of the elongated member 2624. FIG. 31 also shows the pin 2628 extending across the slot 2627 and through slots 2618 and 2608 formed in the first and second shearing parts 2604 and 2614, respectively.

Figure 31A:
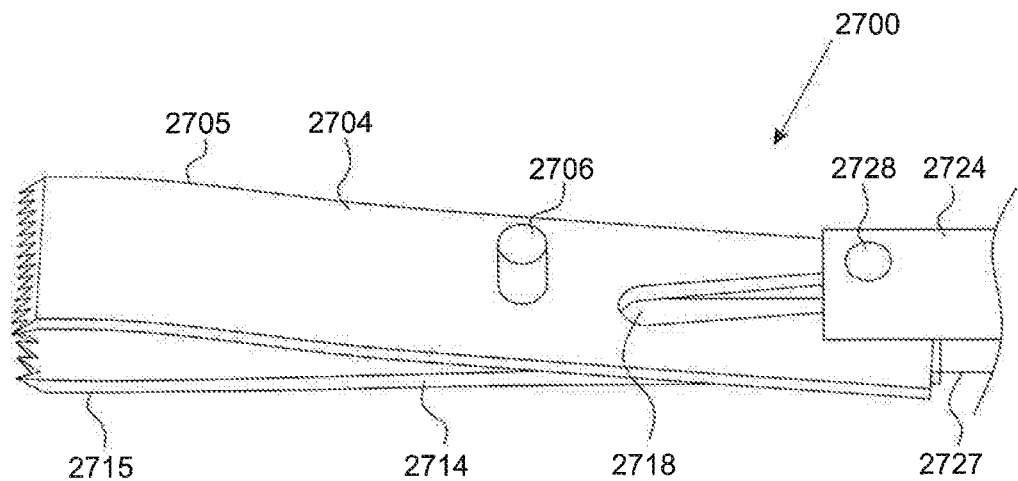
FIGS. 31A-31C are views of another example delamination device.

FIG. 31A shows a perspective view of another delamination device 2700 with a tubular member 2702 (shown in FIG. 31C) removed. The delamination device 2700 is similar to the delamination device 2600 except that first and second shearing parts 2704 and 2714 have curved portions 2705 and 2715, respectively. The first and second shearing parts 2704 and 2714 include a plurality of teeth formed at their respective distal ends. The delamination device 1700 includes an elongated member 2724 disposed in a lumen of the tubular member 2702, similar to the elongated member 2624, described above. The tubular member 2702 is reciprocable within the lumen of the tubular member 2702. Proximal ends of the first and second shearing parts 2704 and 2714 are received into a slot 2727 formed in a distal end of the elongated member 2724. A pin 2728 extends across the slot 2727 and is received in a slot 2718 formed in the first shearing part 2704 and in slot 2710 formed in the second shearing part 2714. The pin 2728 is slideable within the slots 2718 and 2710 in response to movement of the elongated member 2724.

Figure 31B:
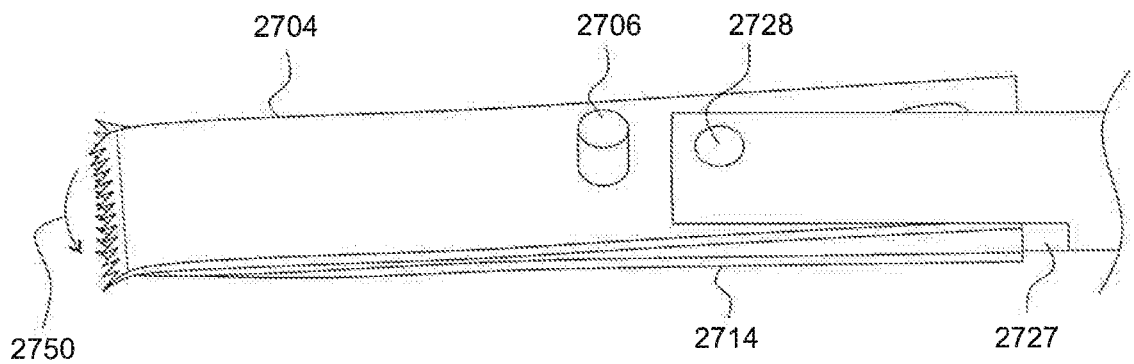
Figure 31C:
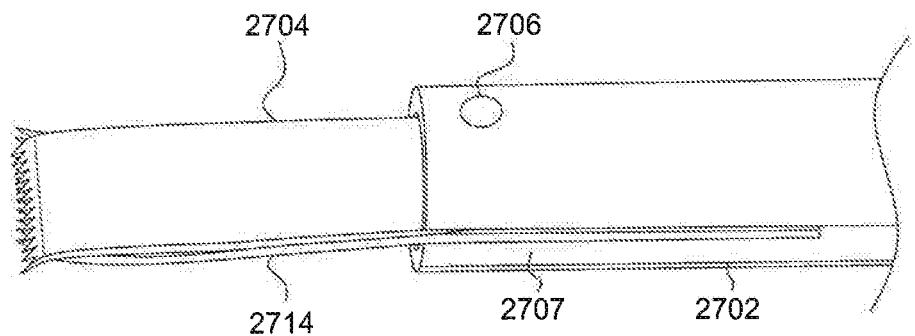

FIG. 31B shows the delamination device 2700 with the elongated member 2624 displaced distally, causing the first shearing part 2704 to pivot in the direction of arrow 2750 as a result of the interaction between the pin 2728 and the slot 2718 formed in the first shearing part 2704. FIG. 31C shows the delamination device 2700 with the tubular member 2702. Similar to the tubular member 2602 discussed above, the tubular member 2702 includes a slot 2707. The slot 2707 provides a relief to receive a proximal end of the first shearing part 2704 as the first shearing part 2704 is reciprocated relative to the pin 2706.

Figure 33:
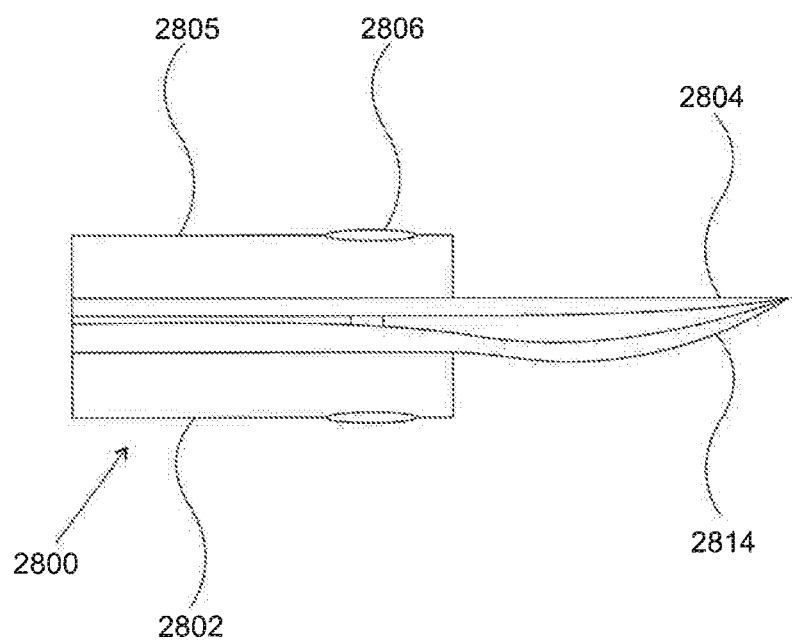
FIG. 33 shows another example delamination device that includes a first shearing part that has a curved shape and a second shearing part that has a flat shape.
Figure 34:
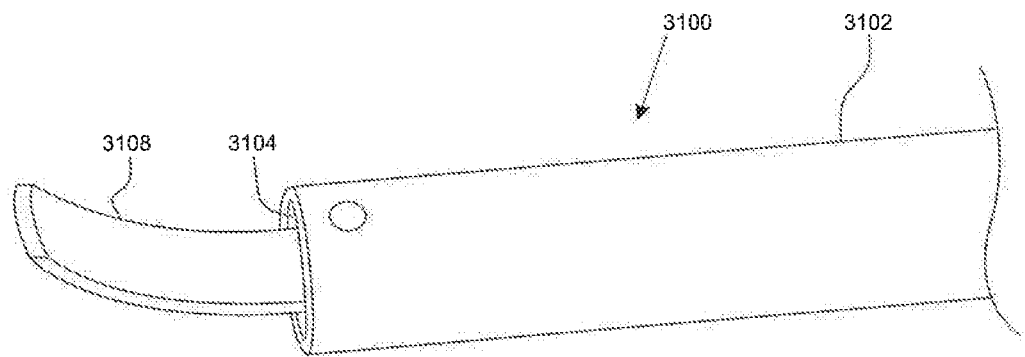
FIGS. 34-37 illustrate another example delamination device.
Figure 35:
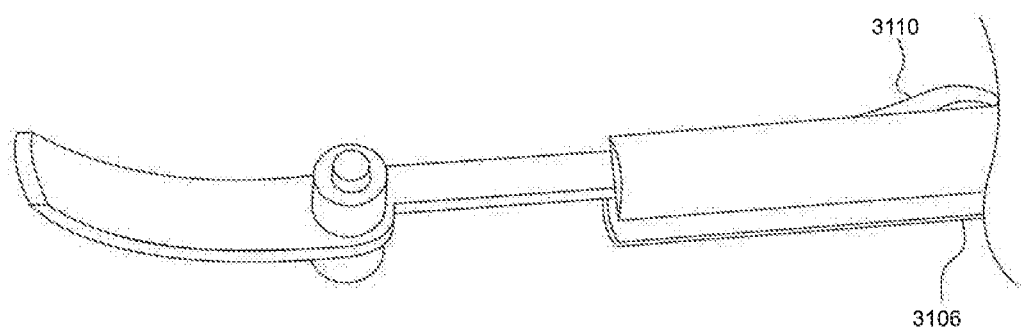

Shearing parts having other shapes are also within the scope of the present disclosure. For example, FIG. 33 shows another example delamination device 2800 that includes a second shearing part 2814 that has a curved shape and a first shearing part 2804 that has a flat shape. The first and second shearing parts 2804 and 2814 are pivotably connected via a pin 2806 to a tubular member 2802. The tubular member 2802 includes a longitudinally extending slot 2805, which may be similar to and perform a similar function as the slot 2605.

Figure 32:
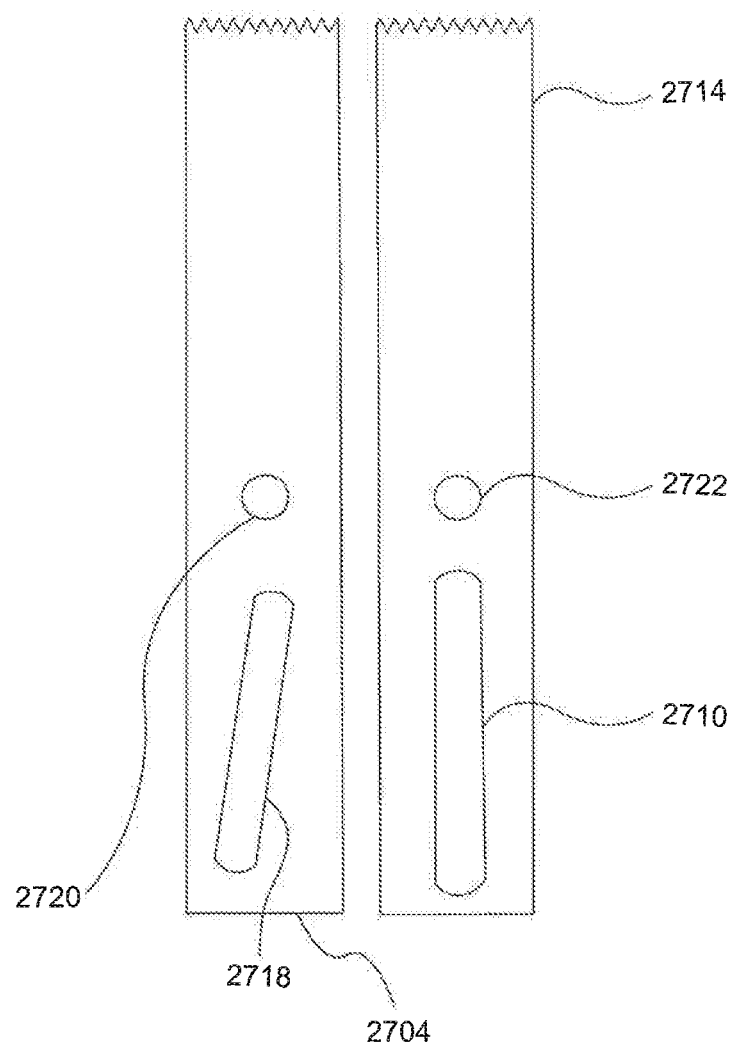
FIG. 32 shows a first shearing part and a second shearing part of the delamination device of FIGS. 31A-31C.

FIG. 32 shows a top view of the example first and second shearing parts 2704 and 2714. The first shearing part 2704 includes an aperture 2720, and the second shearing part 2714 includes an aperture 2722. The apertures 2720 and 2722 align to receive a pin 2706, which may be similar to pin 2606, described above. In some instances, the first shearing part 2704 may be pivotable about the pin 2706. In other instances, the first shearing part 2704 may be rotationally fixed relative to the pin 2706. In such implementations, the pin 2706 and the first shearing part 2704 may pivot relative to the tubular member 2702. FIG. 32 also illustrates a slot 2718 (formed in first shearing part 2704) and a slot 2710 (formed in the second shearing part 2714). The slots 2710 and 2718 may be similar to, and function similarly to, the slots 2610 and 2618, respectively, described above. Particularly, the slots 2710 and 2718 receive a pin 2728, similar to pin 2628, described above, and the pin 2728 is operable to pivot the first shearing part 2704 about pin 2706 and relative to the second shearing part 2714 as the pin 2728 is longitudinally displaced relative to the first and second shearing parts 2704 and 2714.

FIGS. 34-37 illustrate another example delamination device 3100. The delamination device 3100 includes an outer tubular member 3102 that defines a lumen 3104, an elongated member 3106 is moveable within the lumen 3104, and a shearing part 3108. The shearing part 3108 includes a biasing member 3110 and a protrusion 3112. In some instances, the biasing member 3110 may be in the form of an elongated segment extending proximally within the tubular member 3102. An end 3113 of the biasing member 3110 is in sliding contact with an interior surface 3115. The elongated member 3106 includes a plurality of teeth 3114 formed along an interior surface 3116 of the elongated member 3106. The plurality of teeth 3114 engages the protrusion 3112 formed on the shearing part 3108.

Figure 36:
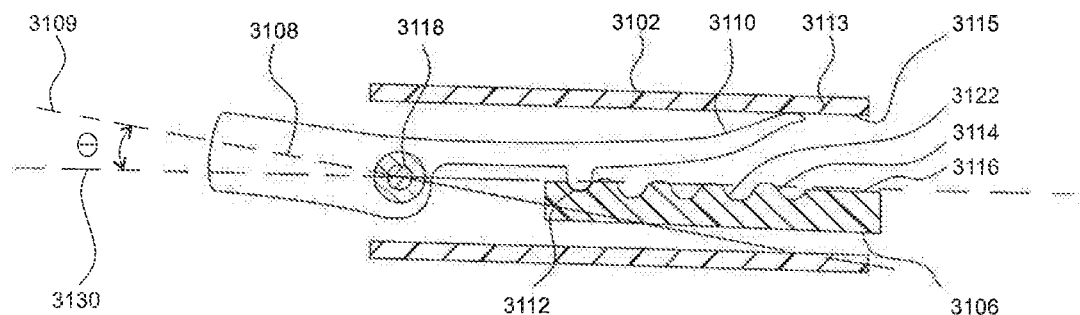
Figure 37:
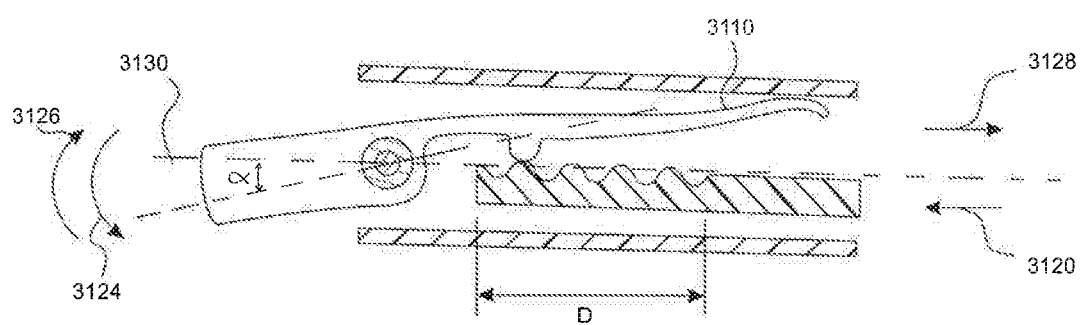

The shearing part 3108 is pivotably connected to the tubular member 3102 via a pin 3118. The shearing part 3108 is pivotable about the pin 3118 relative to the tubular member 3102. Movement of the elongated member 3106 in the direction of arrow 3120 causes the protrusion 3112 to ride along an undulating surface 3122 defined by the plurality of teeth 3114 which, in turn, causes the shearing part 3108 to pivot in an oscillating manner about pin 3118. Referring to FIG. 37, as the protrusion 3112 reaches a peak of one of the teeth 3114, the shearing part 3108 moves in the direction of arrow 3124 and the biasing member 3110 is elastically deformed, producing or increasing a biasing force to return the shearing part 3108 to an initial position, as shown in FIG. 36. As the elongated member 3106 continues to move such that the protrusion 3112 reaches a trough defined by the undulating surface 3122, the shearing part 3108 return to the initial position in the direction of arrow 3126. As the elongated member 3106 is moved alternatingly in the directions of arrows 3120 and 3128, for example, a distance D, the protrusion 3112 moves in an oscillating manner along the undulating surface 3122, causing the shearing part 3108 to move alternatingly in the directions of arrows 3124 and 3126 so as to produce a cutting action.

Although FIG. 36 shows that the shearing part 3108 is substantially aligned with a longitudinal axis 3130 of the delamination device 3100, the angle of the shearing part 3108 relative to the longitudinal axis 3130 may be different in some implementations. For example, in some instances, a longitudinal axis 3109 of the shearing part 3108 and the longitudinal axis 3130 may form an angle θ when the protrusion 3112 resides in a trough of the undulating surface 3122, as shown in FIG. 36. In some implementations, the longitudinal axis 3109 of the shearing part 3108 and the longitudinal axis 3130 may be the same, and hence, the angle formed therebetween is 0°. In other implementations, this angle may be a non-zero value. An angle α may be defined between the shearing part 3108 and the longitudinal axis 3130 when the protrusion 3112 is at a peak of the undulating surface 3122, as shown in FIG. 37. In some implementations, the angle α may be identical to the angle θ defined. Thus, in some instances, the angles θ and α may be the same. In other implementations, angles θ and α may be different. Further, the angles θ and α may be selected to be any desired angle.

Also, although the example delamination device 3100, shown in FIGS. 36 and 37, includes a single shearing part 3108, other implementations may include a second shearing part. For example, in other implementations, a second shearing part may be secured to and stationary relative to the tubular member 3102, such that a first shearing part, similar to shearing part 3108 described above, may be moveable relative to the second shearing part.

Figure 38:
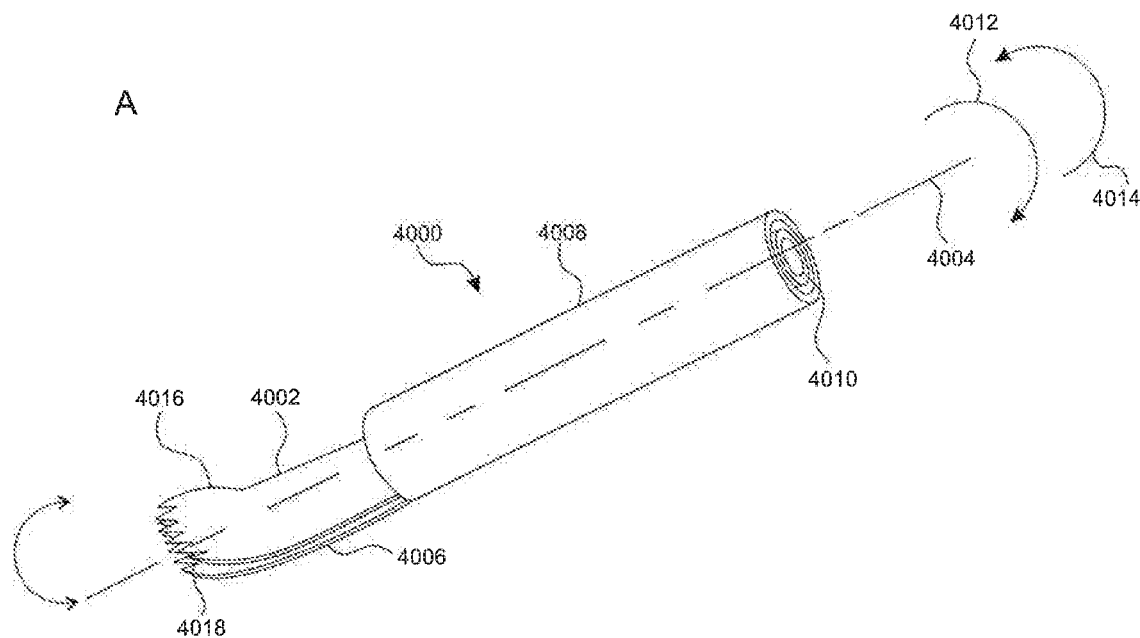
FIG. 38 illustrates another example delamination device having a shearing part rotatable about a longitudinal axis.

FIG. 38 illustrates another example delamination device 4000. The delamination device 4000 includes a first shearing part 4002 that is rotatable about a longitudinal axis 4004 relative to a second shearing part 4006. In the example shown, the first shearing part 4002 and the second shearing part 4006 have shapes that are cylindrical about the longitudinal axis 4004, and each of the first and second shearing parts 4002 and 4006 has a distal end, i.e., distal ends 4016 and 4018, respectively, that curves towards the longitudinal axis 4004. Further, the first shearing part 4002 nests within the second shearing part 4006. Thus, the first shearing part 4002 follows the contour of the second shearing part 4006 when the first shearing part 4002 is rotated relative to the second shearing part 4006.

The delamination device 4000 also includes an outer tubular member 4008 and an inner tubular member 4010 that is rotatable about the longitudinal axis 4004 relative to the outer tubular member 4008. In some implementations, the inner tubular member 4010 is rotated a small angular amount in a reciprocating manner in the directions of arrows 4012 and 4014.

The second shearing part 4006 is attached to and fixed relative to the outer tubular member 4008. The first shearing part 4002 is attached to and rotatable with the inner tubular member 4010. When the inner tubular member 4010 is reciprocated about the longitudinal axis 4004, the first shearing part 4002 rotates relative to the second shearing part 4006, generating a shearing action at the distal ends 4016 and 4018 of the first and second shearing parts 4002 and 4006.

FIG. 38 shows that the distal ends 4016 and 4018 of first and second shearing parts 4002 and 4006, respectively, are serrated forming a plurality of teeth. However, in other implementations, only one shearing parts may include teeth formed on a distal end thereof. In still other implementations, neither of the shearing parts may include teeth. In other implementations, the shearing parts may include a sharpened, tapered leading edge. Still further, one or both of the shearing parts may include any of the types of leading edges described herein.

Figure 39:
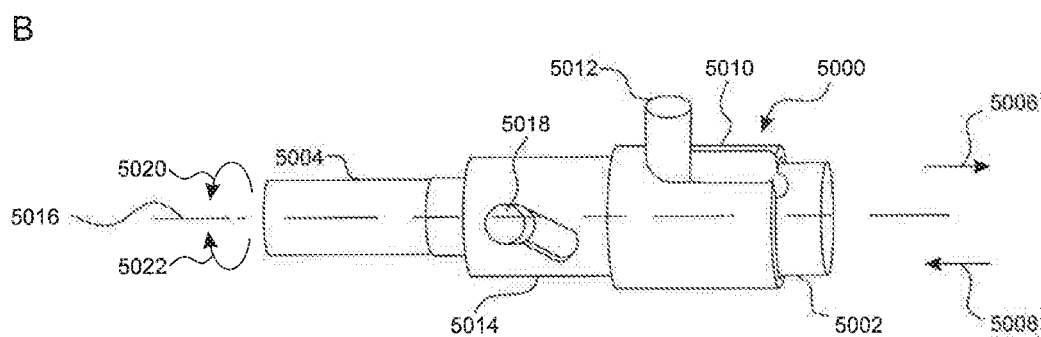
FIG. 39 shows a mechanism that converts a longitudinal movement into a rotational movement.

FIG. 39 shows a mechanism 5000 that converts a longitudinal movement into a rotation. Such a mechanism may be incorporated into a delamination device, such as the delamination device 4000, to produce a reciprocating rotation motion of an inner tubular member and associated shearing part. The mechanism 5000 includes a first part 5002 and a second part 5004 slidingly received into the first part 5002. The first part 5002 is longitudinally reciprocable in the directions of arrows 5006 and 5008. The first part 5002 includes a first slot 5010 that receives a pin 5012. The pin 5012 may be fixedly attached to an outer member, such as an outer tubular member of a type described herein, for example. Cooperation between the pin 5012 and the first slot 5010 defines a rotational orientation of the first part 5002 as the first part 5002 reciprocates. The first slot 5010 may also define a stroke length of the first part 5002 in both the direction of arrows 5006 and 5008, i.e., an amount by which the first part 5002 is permitted to move longitudinally.

The first part 5002 also includes a second slot 5014. The second slot 5014 is formed at an angle relative to a longitudinal axis 5016. The second slot 5014 receives a pin 5016 formed coupled to the second part 5004. In some instances, the pin 5018 may be integrally formed with the second part 5004 or otherwise attached thereto.

In operation, as the first part 5002 moves in the direction of arrow 5008, the pin 5012 maintains rotational positioning of the first part 5002. Further, as the first part moves in the direction of arrow 5008, the pin 5018 is compelled to follow the angular path defined by the second slot 5014. As a result, the second part 5004 rotates in the direction of arrow 5020. When the first part 5002 reverses direction and is displaced in the direction of arrow 5006, the second part 5004 rotates in the direction of arrow 5022 as a result of the interaction between the second slot 5014 and pin 5018. Consequently, as the first part 5002 is reciprocated in the directions of arrows 5006, 5008, the second part 5004 is reciprocated in the directions of arrows 5020 and 5022. Thus, mechanism 5000 functions to convert a linear motion into an angular rotation.

Figure 40:
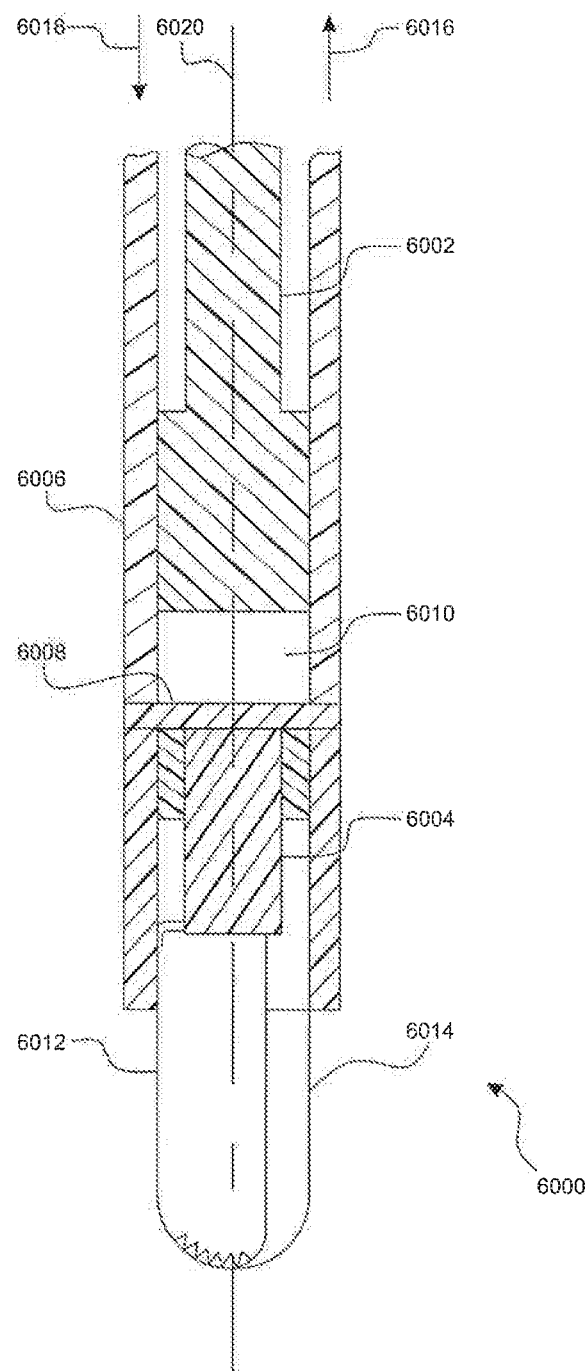
FIG. 40 shows a cross-sectional view of an example delamination device that incorporates a mechanism similar to the mechanism shown in FIG. 39.

FIG. 40 is shows a cross-sectional view of an example delamination device 6000 that incorporates a mechanism similar to the mechanism 5000 described above. The delamination device 6000 includes a first part 6002, a second part 6004, and an outer tubular member 6006. A pin 6008 extends through a slot 6010 formed in the first part 6002. The pin 6008 and the slot 6010 cooperate to rotationally align the first part 6002 and to define a stroke of the first part 6002 as it is reciprocated within the outer tubular member 6006. The first part 6002 also includes a second slot (not shown due to the cross-sectional nature of FIG. 40) that may be similar to the second slot 5014 described above. Similarly, the second part 6004 includes a pin (also not shown due to the cross-sectional nature of FIG. 40), similar to the pin 5018 described above. A first shearing part 6012 is attached to the second part 6004 and moveable therewith. A second shearing part 6014 is attached to the outer tubular member 6006. Thus, when the first part 6002 is reciprocated in the directions of arrows 6016 and 6018, the second part 6004 is rotated in reciprocating manner about longitudinal axis 6020. Being attached to the second part 6004, the first shearing part 6012 similarly rotated in a reciprocating manner about the longitudinal axis 6020. Because the second shearing part 6014 is fixed relative to the tubular housing and because the second part 6004 and first shearing part 6012 rotates relative to the outer tubular housing 6006, the first shearing part 6012 is rotated relative to the second shearing part 6014 to create a shearing action that may be used to remove a membrane from an underlying tissue.

Figure 44:
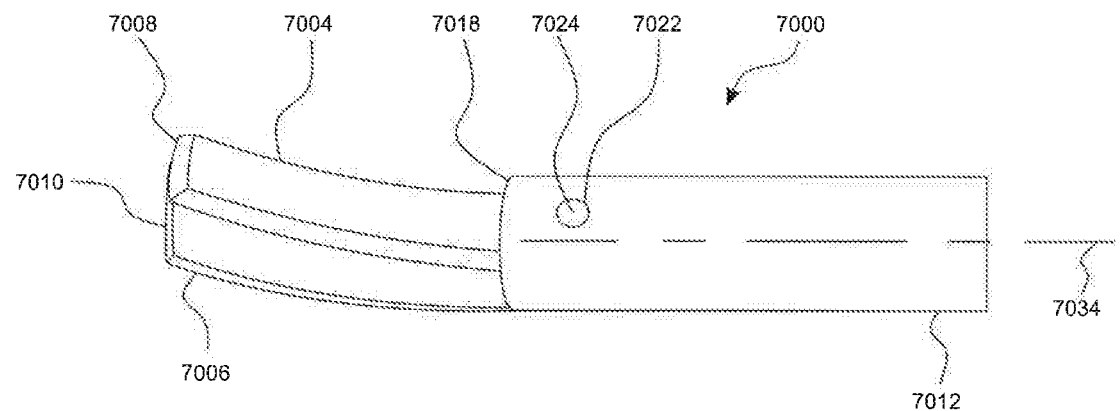
FIGS. 44-46 show another example delamination device.
Figure 45:
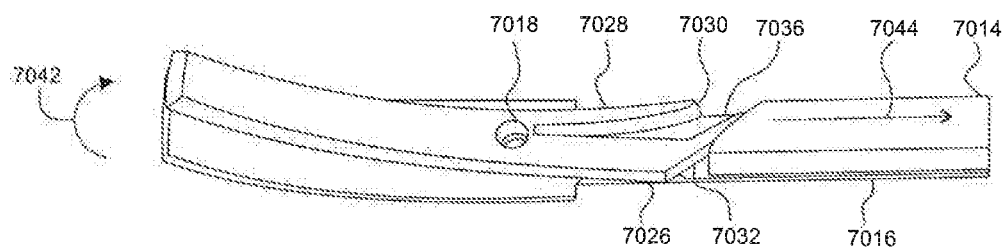
Figure 46:
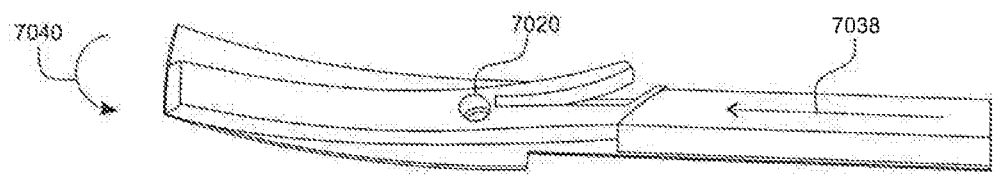

FIGS. 44-46 show another example delamination device 7000 that includes an outer tubular member 7002, a first shearing part 7004, and a second shearing part 7006. The first and second shearing parts 7004 and 7006 are illustrated as having sharpened distal ends 7008 and 7010, respectively. However, the distal ends 7008 and 7010 have a shape or leading edge configuration according to any of the examples described herein. The delamination device 7000 also includes an outer tubular member 7012 and an elongated member 7014 received and moveable within a lumen of the tubular member 7012.

In the example shown, the second shearing part 7006 includes a proximal portion 7016. In some implementations, the proximal portion 7016 may be received into the lumen formed in the tubular member 7012. In other implementations, the tubular member 7012 may include a longitudinal slot that extends from a distal end 7018 of the tubular member 7012. In some instances, the slot may extend through an entire wall thickness of the tubular member, providing communication between the lumen and the exterior of the tubular member 7012. In other implementations, the slot may extend through only a portion of the wall thickness of the tubular member 7012. The proximal end 7016 of the second shearing part 7006 may be received into the slot formed in the tubular member 7012 and secured therewithin. Thus, the second shearing part 7006 may be fixed relative to the tubular member 7012. In other instances, the second shearing part 7006 may be secured to the tubular member 7012 in any other manner, such as by an adhesive, welding, pinned connection, or any other type of connection.

Each of the first shearing part 7004, the second shearing part 7006 and the tubular member 7012 include an aperture, e.g., apertures 7018, 7020, and 7022, respectively. The apertures 7018, 7020, and 7022 are aligned and receive a pin 7024. As a result, the second shearing part 7006 is pivotably connected relative to the first shearing part 7004 and the tubular member 7012.

The first shearing part 7004 includes a proximal part 7026 and a biasing member 7028. Similar to the biasing member 2316 shown in FIGS. 23 and 24, the biasing member 7028 includes a proximal end 7030 that engages an internal surface of the tubular member 7012. In some instances, this internal surface of the tubular member 7012 may define the lumen formed therein. The proximal part 7026 includes an engagement surface 7032. The engagement surface 7032 may be orthogonal relative to a longitudinal axis 7034 of the tubular member 7012. The elongated member 7014 includes an engagement surface 7036 that engages the engagement surface 7032 of the first shearing part 7004. The engagement surface 7036 may have a shape that corresponds to the shape of the engagement surface 7032. Thus, in the example shown, the engagement surface 7036 is also orthogonally configured relative to the longitudinal axis 7034.

When the elongated member 7014 is displaced in a direction of arrow 7038, the engagement surface 7036 of the elongated member 7014 engages the engagement surface 7032 of the first shearing part 7004, the interaction between the two engagement surfaces 7032 and 7036 causes the first shearing part 7004 to pivot in the direction of arrow 7040. In the example shown, the engagement surfaces 7032 and 7036 form inclined planes. As the elongated member 7014 is moved in the direction of arrow 7038, the interaction between the engagement surface 7032 and the engagement surface 7036 causes the engagements surface 7032 to slide relative to the engagements surface 7036. As a consequence, the first shearing part 7004 is pivoted about pin 7024, relative to the elongated member 7014 and the second shearing part 7006. As the first shearing part 7004 pivots in the direction of arrow 7040, the biasing member 7028 is elastically deformed due to contact between proximal end 7030 and the inner surface of the tubular member 7012. The elastic deformation of the biasing member 7028 urges the first shearing part 7004 to rotate in the direction of arrow 7042. When the elongated member 7014 is moved in the direction of arrow 7044, the first shearing part 7004 pivots about the pin 7024 in the direction of arrow 7042 due to the force applied by the biasing member 7028. Consequently, as the elongated member 7014 is reciprocated, the first shearing part 7004 is oscillated about pin 7024 relative to the second shearing part 7006. This relative movement of the first shearing part 7004 relative to the second shearing part 7006 may be used to sever a membrane from an underlying tissue.

Figure 47:
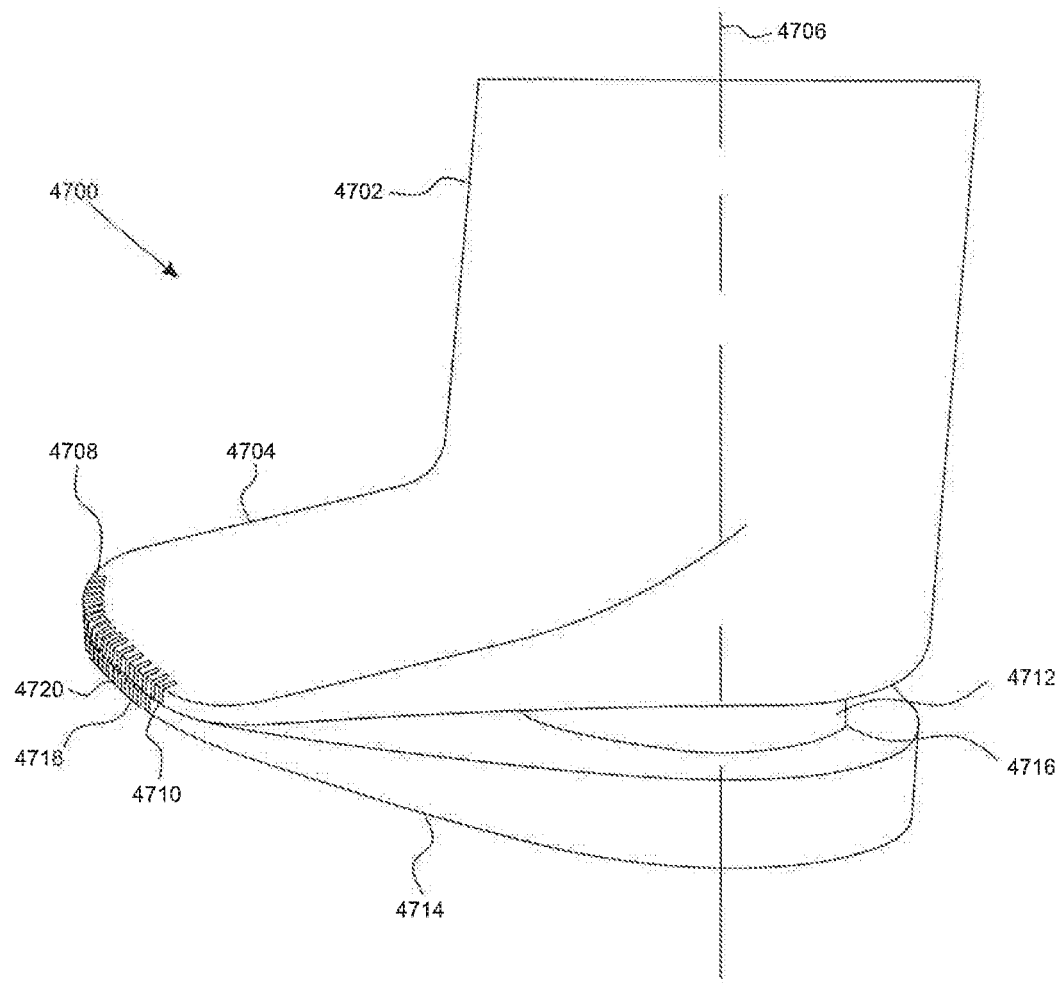
FIG. 47 shows another example delamination device.

FIG. 47 shows another example delamination device 4700. The delamination device 4700 includes a tubular member 4702. In the illustrated example, the tubular member 4702 is shown has having a cylindrical shape with a generally circular cross-sectional shape. However, the tubular member 4702 may have any desired cross-sectional shape. A first shearing part 4704 is integrally formed on the tubular member 4702. In other instances, the first shearing part 4704 may be a separate part that is attached to the tubular member 4702. The first shearing part 4704 extends from the tubular member 4702 at approximately a 90° angle relative to a longitudinal axis 4706 of the delamination device 4700. The first shearing part 4704 includes a plurality of grooves 4708 that define a plurality of teeth 4710.

The delamination device 4700 also includes a shaft 4712 extending through a passage formed in the tubular member 4702. The shaft 4712 and the tubular member 4702 are rotatable relative to each other about the longitudinal axis 4706. A second shearing part 4714 is attached to the shaft 4712 at a distal end 4716 thereof. In some implementations, the second shearing part 4714 may be integrally formed with the shaft 4712. In other implementations, the second shearing part 4714 may be a separate component attached to the shaft 4712. Similar to the first shearing part 4704, the second shearing part 4714 extends from the shaft 4712 at approximately a 90° angle relative to a longitudinal axis 4706 of the delamination device 4700. In other implementations, the angle formed between the first shearing part 4704 and the longitudinal axis 4706 and the angle formed between the second shearing part 4714 and the longitudinal axis 4704 may be within the range of 90° and 180°. In other implementations, these angles may be between 90° and 135°. The second shearing part 4714 includes a plurality of grooves 4718 that define a plurality of teeth 4720.

In operation, the tubular member 4702 may be oscillated about the longitudinal axis 4706 relative to the shaft 4712, which results in the a shearing movement of the first shearing part 4704 relative to the second shearing part 4714. In this manner, the second shearing part 4714 is made stationary relative to an object located adjacent thereto, such as the retina of an eye. In some instances, the angle of rotation of the tubular member 4702 relative to the shaft 4712 may be within the range of three to ten degrees. However, the angle of rotation of the tubular member 4702 relative to the shaft 4712 may be any desired angular amount.

In some instances, a delamination device may include a first shearing part that moves in an axial direction relative to a second shearing part, as opposed to a lateral shearing movement. In one or more of the example delamination devices described herein, one or both of the shearing parts may have a diamond, silicon carbide, or other hard protective coating formed thereon. The coating may be used to prevent wear and reduce friction. Also, in some implementations, the shearing parts of one or more of the example delamination devices described herein may be used to perform diathermy in order, for example, to coagulate vascular tissue that is disposed between the shearing parts. The shearing parts may be insulated as needed in order to transmit radio frequency energy to perform the diathermy function.

Persons of ordinary skill in the art will appreciate that the examples encompassed by the present disclosure are not limited to the particular implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A membrane delamination device comprising:
   a first shearing part;
   a second shearing part pivotably connected to the first shearing part via a pinned connection and comprising a proximal part having a first engagement surface, and further comprising a biasing member extending proximally from the pinned connection;
   a tubular member comprising a lumen adapted to at least partially enclose the first shearing part and the second shearing part; and
   an elongated member adapted to be positioned and moveable within the lumen of the tubular member, the elongated member comprising a second engagement surface configured to engage with the first engagement surface of the second shearing part;
   wherein a distal part of the second shearing part is laterally moveable in a first lateral direction in response to an interaction between the first engagement surface and the second engagement surface; and
   wherein the biasing member is configured to be elastically deformed in response to movement of the distal part of the second shearing part in the first lateral direction to generate a biasing force that urges the distal part of the second shearing part towards a second lateral direction.

2. The membrane delamination device of claim 1, wherein the first engagement surface of the second shearing part is orthogonally configured relative to a longitudinal axis of the tubular member.

3. The membrane delamination device of claim 1, wherein at least one of the first shearing part or the second shearing part includes a plurality of teeth formed along a leading edge thereof.

4. The membrane delamination device of claim 1, wherein at least one of the first shearing part and the second shearing part includes a sharpened leading edge.

5. The membrane delamination device of claim 1, wherein:
   the first shearing part comprises a first aperture, the second shearing part comprises a second aperture, and the tubular member comprises a third aperture; and
   the membrane delamination device further comprises a pin configured to be received through the first aperture, the second aperture, and the third aperture in an aligned configuration, such that the second shearing part is pivotably connected relative to the first shearing part and the tubular member.

6. The membrane delamination device of claim 1, wherein the first engagement surface of the second shearing part is configured to slide relative to the second engagement surface of the elongated member, thereby causing the second shearing part to pivot relative to the elongated member and the first shearing part.

* * * * *